United States Patent
Ding

(10) Patent No.: US 7,900,614 B2
(45) Date of Patent: Mar. 8, 2011

(54) SELF-CALIBRATING $NO_x$ SENSOR

(75) Inventor: Yi Ding, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 387 days.

(21) Appl. No.: 12/125,755

(22) Filed: May 22, 2008

(65) Prior Publication Data

US 2009/0288469 A1 Nov. 26, 2009

(51) Int. Cl.
*F02D 41/00* (2006.01)
*F02D 41/06* (2006.01)
*G01N 27/00* (2006.01)
*F01N 11/00* (2006.01)

(52) U.S. Cl. ........ 123/672; 73/1.07; 73/114.71; 123/685; 123/693

(58) Field of Classification Search .................. 123/672, 123/674, 679, 685, 693
See application file for complete search history.

(56) References Cited

U.S. PATENT DOCUMENTS

| | | | | |
|---|---|---|---|---|
| 4,770,760 A | * | 9/1988 | Noda et al. | 204/425 |
| 4,831,257 A | * | 5/1989 | McClelland et al. | 250/338.1 |
| 6,059,947 A | * | 5/2000 | Kato et al. | 204/425 |
| 6,099,717 A | | 8/2000 | Yamada et al. | |
| 6,363,715 B1 | * | 4/2002 | Bidner et al. | 60/285 |
| 6,375,828 B2 | * | 4/2002 | Ando et al. | 205/781 |
| 6,720,534 B2 | | 4/2004 | Hada et al. | |
| 6,895,800 B2 | | 5/2005 | Tomura et al. | |
| 6,901,745 B2 | * | 6/2005 | Schnaibel et al. | 60/285 |
| 6,901,795 B2 | | 6/2005 | Naguib et al. | |
| 7,721,529 B2 | * | 5/2010 | Kesse et al. | 60/277 |
| 2009/0158706 A1 | * | 6/2009 | Sun | 60/274 |

FOREIGN PATENT DOCUMENTS

| | | | |
|---|---|---|---|
| DE | 10014881 A1 | * | 9/2001 |
| DE | 10309422 A1 | * | 9/2004 |
| JP | 11101154 A | * | 4/1999 |
| JP | 2008002272 A | * | 1/2008 |
| WO | WO0055614 A1 | * | 9/2000 |
| WO | WO0076636 A1 | * | 12/2000 |

* cited by examiner

*Primary Examiner* — Thomas P Noland
(74) *Attorney, Agent, or Firm* — Julia Voutyras; Alleman Hall McCoy Russell & Tuttle LLP

(57) ABSTRACT

A system for calibrating a response to an exhaust-stream $NO_x$ level in a motor vehicle is provided. The system comprises a $NO_x$ sensor that includes an electrode, a current from the electrode responsive to the exhaust-stream $NO_x$ level while a bias voltage is applied to the electrode. The system further comprises a controller configured to interrupt the bias voltage and to adjust a motor-vehicle response to the current based at least partly on an attained voltage of the electrode while the bias voltage is interrupted. Other embodiments provide a method of calibrating a $NO_x$ sensor response in terms of gain and offset parameters.

22 Claims, 3 Drawing Sheets

SELF-CALIBRATING $NO_x$ SENSOR

TECHNICAL FIELD

The present application relates to emissions control in motor vehicles, and more particularly, to nitrogen oxide ($NO_x$) emissions from motor vehicles.

BACKGROUND AND SUMMARY

Various emissions from motor-vehicle exhaust systems are regulated, such as $NO_x$ emission. To limit $NO_x$ emission while maintaining performance, a motor-vehicle may be configured, in a closed-loop manner, to tighten emission control when an exhaust-stream $NO_x$ level increases. Tightening control may include, for example, supplying a richer air/fuel mixture to a combustion chamber of the motor vehicle or enabling reductive regeneration of an exhaust-stream $NO_x$ trap.

For some control systems to function effectively, an accurate estimate of the $NO_x$ level may be generated from a $NO_x$ sensor. U.S. Pat. No. 4,770,760 describes a $NO_x$ sensor comprising two electrochemical pump cells in series, with a diffusion restrictor upstream of each pump cell. In the cited reference, the $NO_x$ level in an analyte is indicated by a diffusion-limited current flowing to a catalyzed electrode in a downstream pump cell, an upstream pump cell being used to reduce the partial pressure of oxygen ($O_2$) to a fixed, low level, so that the $NO_x$ level can be estimated with a minimum of interference.

In the decade since this technology was developed, numerous attempts have been made to improve the accuracy, reliability, and longevity of electrochemical $NO_x$ sensors. For example, U.S. Pat. No. 6,059,947 describes a $NO_x$ sensor providing feedback control of a set-point voltage in the upstream pump cell, and a self-diagnosis feature coupled to the feedback control. The feedback control adjusts the set-point voltage so that the partial pressure of $O_2$ in the second pump cell remains constant despite aging of sensor components and changes in analyte $O_2$ level. The self-diagnosis feature compares the adjusted set point against predetermined limits to assess sensor degradation.

However, the above reference fails to address other ageing effects commonly observed in electrochemical $NO_x$-sensor response: namely, a gradual reduction in gain and an increase in offset in the correlation between the sensed parameters and $NO_x$ in the exhaust stream. These factors, which contribute to uncertainty in the detected $NO_x$ level, may be caused by degradation losses occurring on prolonged operation of the $NO_x$ sensor: losses in electrolyte conductance, for example, or in electroactivity and/or electroactive surface area of one or more electrodes.

The inventors herein have recognized the above problems and have devised a series of approaches to address them. Thus, in one embodiment, a system for calibrating a response to an exhaust-stream $NO_x$ level in a motor vehicle is provided. The system comprises a $NO_x$ sensor that includes an electrode, a current from the electrode responsive to the exhaust-stream $NO_x$ level while a bias voltage is applied to the electrode. The system further comprises a controller configured to interrupt the bias voltage and to adjust a motor-vehicle response to the current based at least partly on an attained voltage of the electrode while the bias voltage is interrupted.

By calibrating the motor-vehicle response based on the attained voltage, the motor-vehicle response may track the exhaust-stream $NO_x$ level with greater fidelity despite degradation losses in the $NO_x$ sensor, such as those indicated above.

Other embodiments disclosed herein provide a method of calibrating a response to an exhaust-stream $NO_x$ level in a motor vehicle. Still other embodiments provide a method of calibrating the $NO_x$ sensor response in terms of gain and offset parameters.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
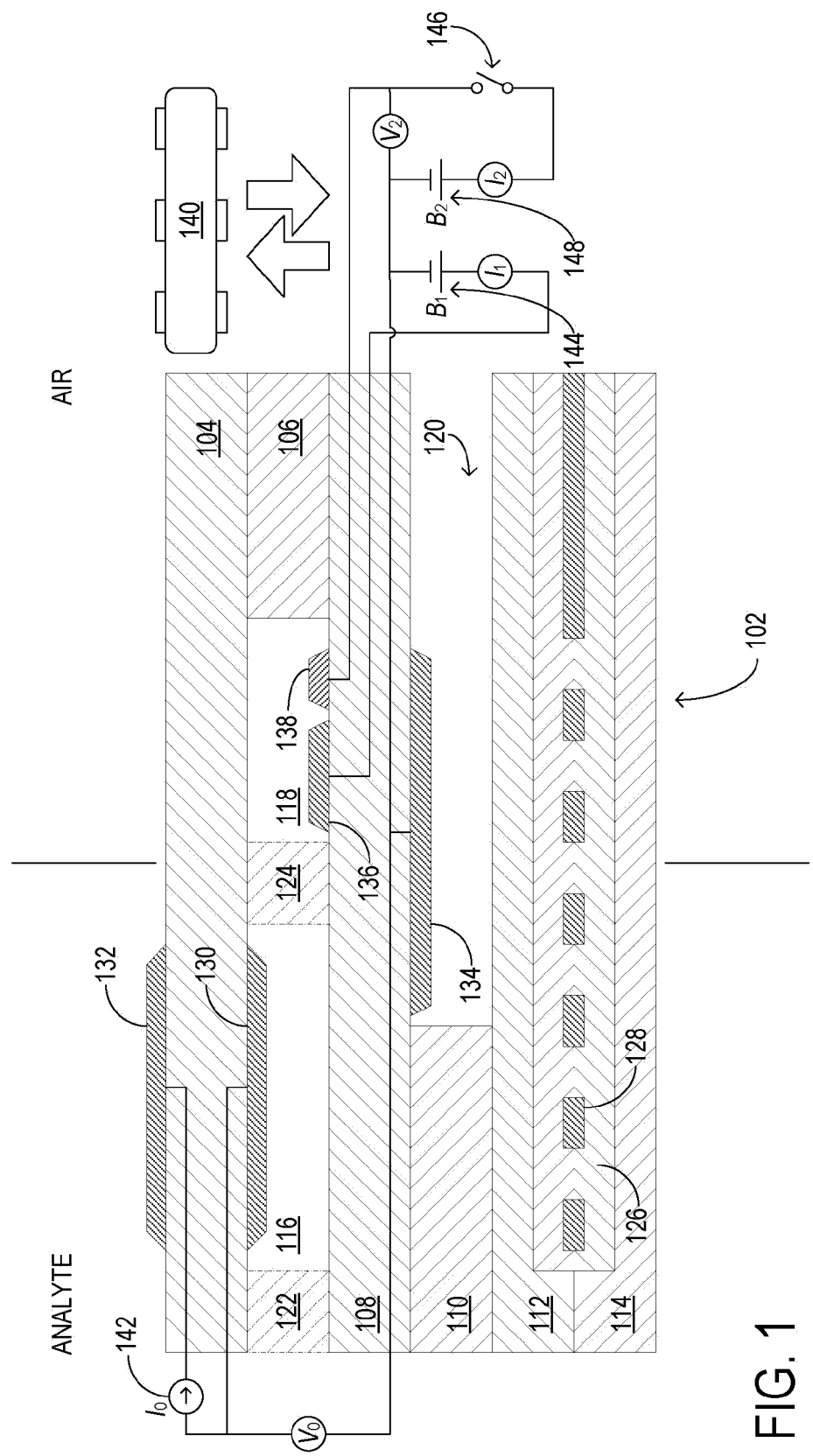
FIG. 1 shows a $NO_x$ sensor with associated control and measurement electronics in accordance with the present disclosure. The drawing is schematic and renders the $NO_x$ sensor in cross section.

FIG. 1 shows a schematic, cross-sectional view of an example $NO_x$ sensor. In particular, FIG. 1 shows $NO_x$ sensor 102 comprising first layer 104, second layer 106, third layer 108, fourth layer 110, fifth layer 112, and sixth layer 114. At least the first and third layers comprise an oxide ($O^{2-}$) conducting solid electrolyte material, e.g., a zirconia ($ZrO_2$) containing ceramic. The remaining layers may comprise the same and/or different materials: other ceramics, for example, selected to bond reliably to the first and third layers, to have similar coefficients of thermal expansion, etc.

$NO_x$ sensor 102 further includes upstream cavity 116, downstream cavity 118, reference cavity 120, first diffusion restrictor 122, and second diffusion restrictor 124. Each of the upstream, downstream, and reference cavities is a void space formed in the layered structure of the $NO_x$ sensor and configured to confine a specimen of gas. In particular, upstream cavity 116 and downstream cavity 118 are configured to confine analyte-derived gas, and reference cavity 120 is configured to confine air. It will be understood that 'confine,' as used in this context, need not imply long-term confinement. In the illustrated embodiment, air may enter the reference cavity from the right side exterior the sensor.

First diffusion restrictor 122 is a material zone that restricts a diffusion of analyte gas into the upstream cavity. In the illustrated embodiment, analyte gas, which may include gas from a motor-vehicle exhaust stream, may penetrate the first diffusion restrictor from the left side exterior the sensor. First diffusion restrictor 122 may include one or more small apertures through which analyte gas may communicate with the upstream cavity; it may be a porous material including but not limited to a porous $ZrO_2$-containing ceramic. Second diffusion restrictor 124 is a material zone that restricts a diffusion of gas from the upstream cavity to the downstream cavity. The second diffusion restrictor may be substantially the same or at least partly different than the first diffusion restrictor.

$NO_x$ sensor 102 further includes insulator 126 and resistive heater 128. Insulator 126 is an electrically insulating and ionically insulating material, e.g., a ceramic such as alumina, selected to bond reliably to the first and third layers, to have similar coefficients of thermal expansion, etc. Insulator 126 may include a groove into which resistive heater 128 is entrained. Resistive heater 128 is a resistive, electrical conductor configured to support a flow of current and thereby to supply heat to $NO_x$ sensor 102.

$NO_x$ sensor 102 further includes upstream cathode 130, upstream anode 132, and reference electrode 134. Each of the upstream cathode, the upstream anode, and the reference electrode may be a porous cermet-type electrode. Each may include a corrosion-resistant, refractory metal such as a platinum-group metal and a ceramic selected to bond reliably to the first and third layers, to have similar coefficients of thermal expansion, etc. In a manner well-known in the art, a formulation of upstream cathode 130 may be selected for its lack of catalytic activity toward $NO_x$.

$NO_x$ sensor 102 further includes downstream cathode 136 and $NO_x$-sensing electrode 138. Each of the downstream cathode and the $NO_x$-sensing electrode may be substantially the same or at least partly different than the electrodes described above. However, a formulation of $NO_x$-sensing electrode 138 may be selected, in a manner well-known in the art, especially for its significant catalytic activity toward $NO_x$.

FIG. 1 shows example control and measurement electronics operatively coupled to $NO_x$ sensor 102. In FIG. 1, some of the control and measurement electronics are shown in schematic detail; the rest are referred to collectively as $NO_x$-sensor controller 140. It must be understood, however, that this distinction is for illustrative purposes only, as any control or measurement component described herein may be integrated into, or located outside of, any motor-vehicle control device.

FIG. 1 shows current source 142, which draws current $I_0$ from upstream cathode 130 and supplies the same current to upstream anode 132. Note that the direction of current flow, by convention, is opposite the flow of electrons and other negative charge carriers. Thus, the current $I_0$ is such as to reduce molecular oxygen ($O_2$) at upstream cathode 130, to carry the $O^{2-}$ so formed through first layer 104, and to oxidize the $O^{2-}$ back to $O_2$ at upstream anode 132. Upstream cathode 130, upstream anode 132, and intervening first layer 104 are therefore configured to pump $O_2$ out of upstream cavity 116. Collectively, the upstream cathode, the upstream anode, and the first layer are referred to as the upstream pump cell.

By pumping $O_2$ out of upstream cavity 116 faster than it can enter through diffusion restrictor 122, the upstream pump cell may reduce the partial pressure of $O_2$ in the upstream cavity relative to that of the analyte. As an approximation, and subject to conditions and assumptions well-known in the art, the partial pressure of $O_2$ in the upstream cavity is given by a Nernst relation:

$$V_0 = RT \ln(s_{130}/s_{134})/2F = RT \ln(p_{116}/p_{120})/2F \quad (1)$$

In eq 1, $V_0$ is a voltage measured between upstream cathode 130 and reference electrode 134, R is the gas constant, T is the absolute temperature, F is Faraday's constant, $s_{130}$ is the concentration of $O_2$ sorbed on upstream cathode 130, $s_{143}$ is the concentration of $O_2$ sorbed on reference electrode 134, $p_{116}$ is the partial pressure of $O_2$ in upstream cavity 116, and $p_{120}$ is the partial pressure of $O_2$ in reference cavity 120. The right-hand side of eq 1 recognizes that a rapid equilibrium exchanges sorbed and gas-phase $O_2$ in the upstream cavity. Thus, $NO_x$-sensor controller 140 may be configured to dynamically adjust the value of $I_0$ to maintain a constant value of $V_0$, which may correspond to a constant, low value of $p_{116}$.

In that way, the partial pressure of $O_2$ in upstream cavity 116 may be maintained at a constant, low value.

FIG. 1 shows first voltage source 144, which provides bias voltage $B_1$ between downstream cathode 136 and reference electrode 134. The magnitude of bias voltage $B_1$ may be such that reduction of $O_2$ at the downstream cathode is diffusion-limited. Thus, $O_2$ is reduced just as fast as it can diffuse to the downstream cathode, which is the rate at which it penetrates second diffusion restrictor 124. Therefore, the partial pressure of $O_2$ in downstream cavity 118 is maintained at a constant level, lower than the level in upstream cavity 116. Downstream cathode 136, reference electrode 134, and intervening third layer 108 are configured to pump $O_2$ out of downstream cavity 118; collectively, these components are referred to as the downstream pump cell.

FIG. 1 shows switch 146 and second voltage source 148. When switch 146 is closed, second voltage source 148 provides bias voltage $B_2$ between $NO_x$-sensing electrode 138 and reference electrode 134. $NO_x$-sensor controller 140 may be configured to close switch 146 to provide or restore bias voltage $B_2$ and to open switch 146 to interrupt bias voltage $B_2$. Thus, switch 146 may be any electrically controllable switch, whether electromechanical or semiconductor-based.

The magnitude of bias voltage $B_2$ may be such that reduction of $O_2$ at $NO_x$-sensing electrode 138 is diffusion-limited. However, the flux of $O_2$ to the $NO_x$-sensing electrode may be quite small because of the small size of this electrode relative to downstream cathode 136 and because it is located farther from second diffusion restrictor 124. In the illustrated embodiment, $O_2$-reduction current observed at the $NO_x$-sensing electrode corresponds to an interference, i.e., an offset, in the current-based $NO_x$ estimate to be described presently. Reduction of other chemical species, e.g. water, may further contribute to the offset.

As indicated above, $NO_x$-sensing electrode 138 differs from downstream cathode 136 not only in size and location, but also in catalyst loading. In particular, the $NO_x$-sensing electrode is configured to be significantly catalytic toward $NO_x$ while the downstream cathode is configured to be minimally catalytic toward $NO_x$. Thus, the chemical constituents of $NO_x$ may be electrochemically reduced at the $NO_x$-sensing electrode, e.g., $$NO_2 + 2e^- \rightarrow NO + O^{2-}, \text{ and} \quad (2)$$

$$2NO + 4e^- \rightarrow N_2 + 2O^{2-}. \quad (3)$$

In addition, the chemical constituents of $NO_x$ may be decomposed at the $NO_x$-sensing electrode, e.g., $$2NO_2 \rightarrow 2NO + O_2, \text{ and} \quad (4)$$

$$2NO \rightarrow N_2 + O_2, \quad (5)$$

to yield sorbed $O_2$, which in turn may be reduced at the $NO_x$-sensing electrode. Whether by catalyzed electrochemical reduction, by catalyzed decomposition followed by electrochemical reduction, or by some combination of these, the current $I_2$ may therefore reflect a level of $NO_x$ in the analyte over and above the offset. For example, $$I_2 = Gp + H, \quad (6)$$

where p is a partial pressure of a $NO_x$ constituent: nitric oxide (NO), nitrogen dioxide ($NO_2$), dinitrogen tetraoxide ($N_2O_4$), or nitrous oxide ($N_2O$), as examples; G is the sensor gain with respect to that constituent, and H is the sensor offset. In examples where the analyte is derived from motor-vehicle exhaust and may include different $NO_x$ constituents simultaneously, a composite sensor gain may be defined based on predicted proportions of the various $NO_x$ constituents in the exhaust.

On prolonged use, however, the gain and offset of the $NO_x$ sensor may both change. Changes in these parameters may result from an ageing of various sensor components: electrodes, diffusion restrictors, and electrolyte layers, for example. To compensate for changing sensor gain and sensor offset, $NO_x$-sensor controller 140 may be further configured to enable self-calibration of $NO_x$ sensor 102.

Thus, when switch 146 is open, bias voltage $B_2$ to $NO_x$-sensing electrode 138 is interrupted. Under such conditions, the voltage measured between the $NO_x$-sensing electrode and the reference electrode is given by another Nernst relation. As an approximation, and subject to conditions and assumptions well-known in the art, $$V_2 = RT \ln(s_{138}/s_{134})/2F. \tag{7}$$

In eq 6, $s_{138}$ refers to the concentration of $O_2$ sorbed on $NO_x$-sensing electrode 138. Due to the catalyst loading of $NO_x$-sensing electrode 138, $s_{138}$ may not be related in a straightforward way to the partial pressure of $O_2$ in the cavity in which the electrode is disposed—in contrast to eq 1. This is because $NO_x$ decomposition (eqs 4 and 5, for example) supplies additional $O_2$ to the surface of $NO_x$-sensing electrode 138 at a rate that may exceed the rate of exchange of sorbed and gas-phase $O_2$. Thus, $s_{138}$ may increase with increasing $NO_x$ level in the analyte.

An open-circuit or near open-circuit $V_2$ measurement may therefore provide an independent, calibrating estimate of the $NO_x$ level, against which the $I_2$-based estimate may be compared. In one example, a periodically acquired $V_2$-based estimate of the $NO_x$ level may be used to refine gain and offset parameters used in the $I_2$-based estimate.

To enable self calibration, $NO_x$-sensor controller 140 may include analog electronics comprising operational amplifiers, for example, and/or digital electronics comprising a memory, a microprocessor, a look-up table, and/or other components known in the art to enable fixed-function calculation, parameter storage, and/or adjustable-gain amplification. $NO_x$-sensor controller 140 may further include appropriate timing componentry to enable collection of multiple voltage samples according to a schedule.

The example configuration illustrated in FIG. 1 may be used as part of an emissions-control system of a motor vehicle. FIG. 1 illustrates, in one specific example, a $NO_x$-sensor including an electrode, where a current from the electrode may be responsive to an exhaust-stream $NO_x$ level in a motor vehicle while a bias voltage is applied to the electrode. In many instances, the motor vehicle in which the $NO_x$ sensor is installed may be configured to respond in some way to the current. For example, the motor-vehicle response to the current may include reducing a $NO_x$ emission in response to the current. Reducing the $NO_x$ emission may take several different forms depending on the particular motor-vehicle configuration. In some embodiments, the motor vehicle response to the current may include regenerating an exhaust-aftertreatment device in response to the current. In other examples, the motor-vehicle response to the current may include reducing an air-to-fuel ratio in a combustion chamber in response to the current.

Figure 2:
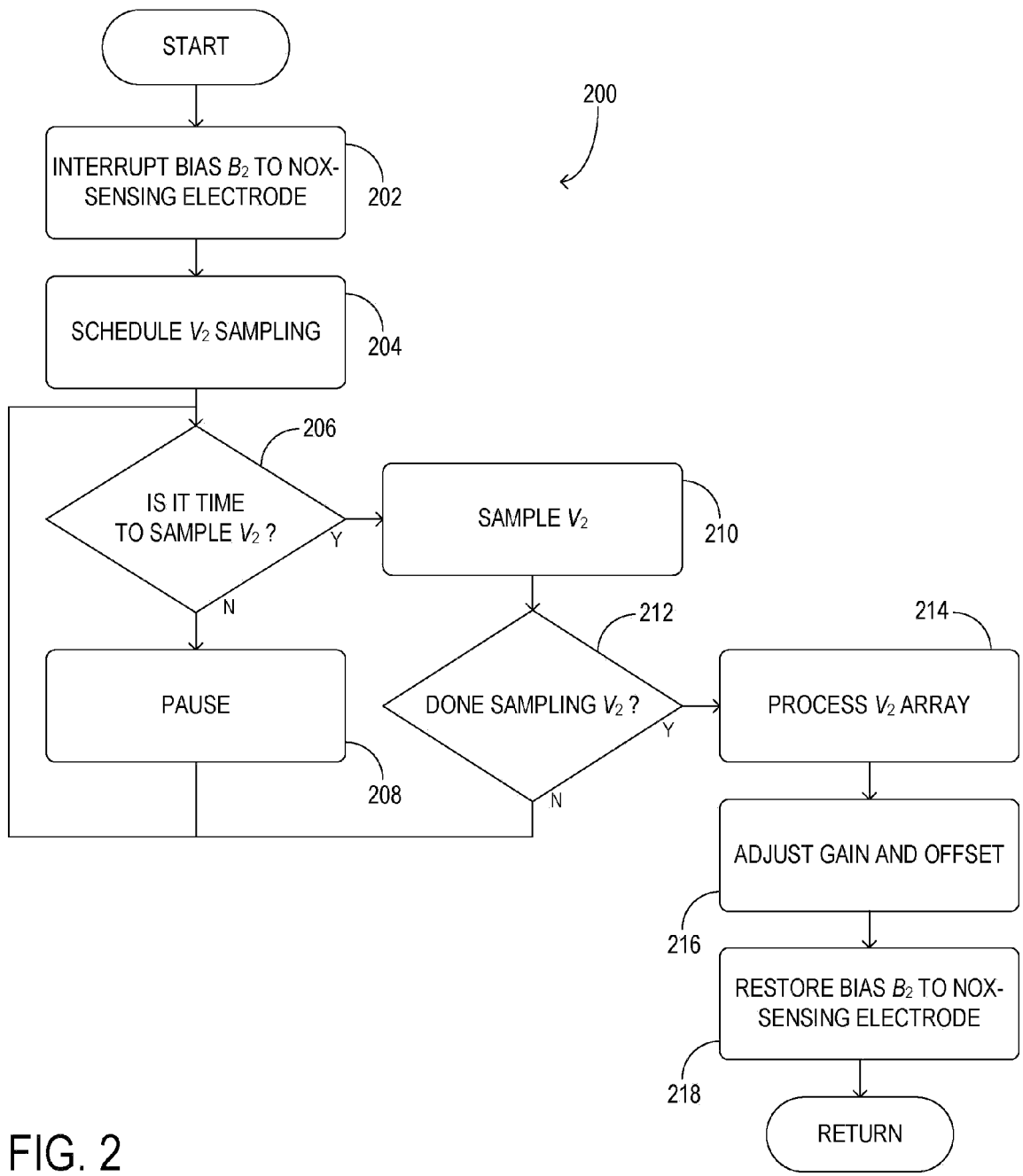
FIG. 2 is a flow chart illustrating an example $NO_x$-sensor self-calibration procedure in accordance with the present disclosure.
Figure 3:
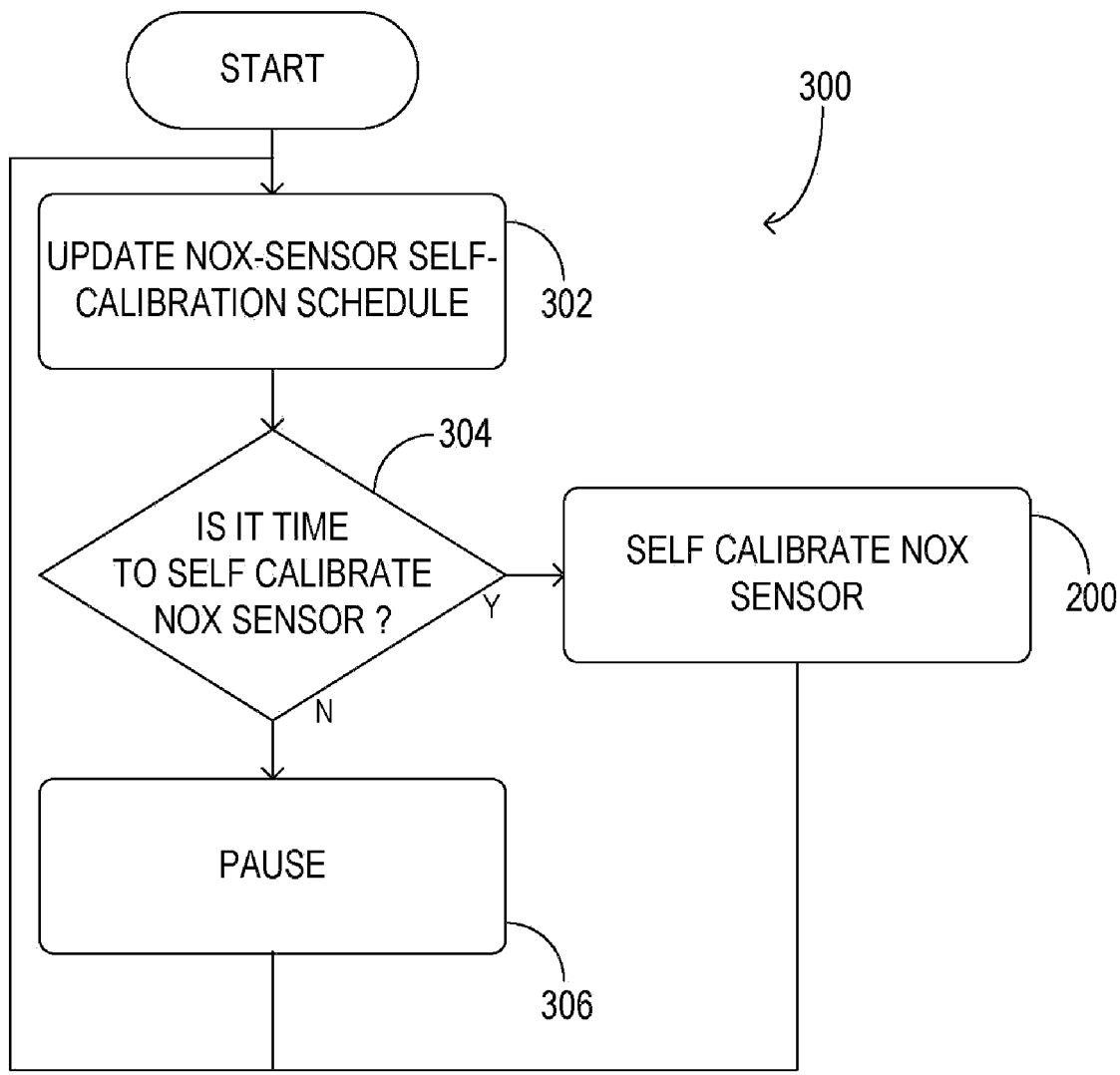
FIG. 3 is a flow chart illustrating an emissions-control procedure, which includes a $NO_x$-sensor self-calibration procedure, in accordance with the present disclosure.

In each of these embodiments, a controller may be further configured to adjust the motor-vehicle response to the current based at least partly on an attained voltage of the electrode during a period in which the bias voltage is interrupted ($V_2$ in the illustrated embodiment). In one example, the controller may do so by refining the $NO_x$-sensor gain and offset parameters used in an emission-control operation, based on the attained voltage. This is an example of $NO_x$-sensor self-calibration, details of which are described below, with reference to FIGS. 2 and 3. FIG. 2 illustrates an example $NO_x$-sensor self-calibration procedure, while FIG. 3 illustrates a manner in which $NO_x$-sensor self calibration may be incorporated into an emissions-control strategy of a motor vehicle.

FIG. 2 is a flow chart illustrating example $NO_x$-sensor self-calibration procedure 200. Procedure 200 is one example of a method of calibrating a response to an exhaust-stream $NO_x$ level in a motor vehicle, where the motor vehicle includes a $NO_x$ sensor. The method includes interrupting a bias voltage to an electrode of the $NO_x$ sensor, a current from the electrode responsive to the exhaust-stream $NO_x$ level absent said interrupting. The method further includes adjusting a motor-vehicle response to the current based at least partly on an attained voltage of the electrode during said interrupting. More particularly, procedure 200 includes adjusting a gain and an offset of the $NO_x$ sensor based at least partly on an attained voltage of the electrode during said interrupting.

In describing procedure 200, continued reference is made to the components of FIG. 1. The procedure may be executed by an emissions-control system of a motor vehicle in a manner illustrated in FIG. 3.

At 202, $NO_x$-sensor controller 140 interrupts bias voltage $B_2$ to $NO_x$-sensing electrode 138. The $NO_x$ sensor controller may interrupt the bias by opening switch 146, for example. When bias voltage $B_2$ is interrupted, current $I_2$ ceases to reflect the $NO_x$ level in the analyte. At 204, $NO_x$-sensor controller 140 schedules a sampling of voltage $V_2$ over a predetermined period of time. In one non-limiting and purely illustrative example, $NO_x$-sensor controller 140 may schedule fifty $V_2$ samples to be recorded at open-circuit, over a period of 25 seconds, at evenly-spaced, 500-millisecond intervals. Details of the scheduling may differ from one motor-vehicle system to the next, and may also depend on operating conditions. For example, when a previous $I_2$ measurement has indicated that the exhaust-stream $NO_x$ level is relatively high, the sampling period may be relatively short. In contrast, when a previous $I_2$ measurement has indicated that the $NO_x$ level is relatively low, the sampling period may be relatively long. Thus the duration of bias voltage interruption and voltage sampling may be responsive to $I_2$. A greater sampling period may be advantageous when the $NO_x$ level is low because more time may be needed for sorbed, active species on $NO_x$-sensing electrode 138 to come to equilibrium with gas-phase $NO_x$ in downstream cavity 118.

At 206, $NO_x$-sensor controller 140 determines whether it is time to record a $V_2$ sample. If it is not time to record a $V_2$ sample, then execution of procedure 200 pauses, at 208, for a predetermined period of time. It should be understood that 'pause,' used herein, implies only that the illustrated procedure is paused. Execution of other related and/or unrelated control routines may continue, and in some embodiments, step 208 may include a programmed interrupt to other such control routines. After the pause, execution resumes at 206, where the $NO_x$-sensor controller again determines if it is time to sample $V_2$. If it is time to sample $V_2$, then at 210, the $NO_x$-sensor controller samples $V_2$. $V_2$ may be sampled at or near open-circuit to avoid concentration polarization in layer 108 at an interface with $NO_x$-sensing electrode 138.

After $V_2$ is sampled, the $NO_x$-sensor controller determines, at 212, whether $V_2$-sampling is completed or whether further sampling is required. The $NO_x$-sensor controller may make the determination based on the time, a number of samples recorded, etc. If $V_2$-sampling is not completed, then execution resumes at 206; if $V_2$-sampling is completed, then execution continues to 214, where the recorded $V_2$ array is processed. In one example, processing the $V_2$ array may include fitting $V_2$-versus-time data to a predicted mathematical model, i.e., a curve, such as an exponential decay. From the fitted model parameters, it may be possible to estimate a steady-state value of $V_2$ at the analyte $NO_x$ level, even if $V_2$ sampling is stopped before the steady-state is reached. Thus, the $NO_x$-sensor controller may be configured to extrapolate to a steady-state value of $V_2$. In other embodiments, the $NO_x$-sensor controller may be configured to discard $V_2$ samples in a period over which $V_2$ is trending rapidly, and to average $V_2$ samples in a period over which $V_2$ is substantially constant, is deviating randomly, and/or is trending slowly.

Processing the $V_2$ array may further include relating the steady-state or average $V_2$, as obtained above, to a predicted, analyte $NO_x$ level. The predicted $NO_x$ level may be obtained from $V_2$ by using a calculation executed by $NO_x$-sensor controller 140, a look-up table, etc.

At 216, the $NO_x$ level so obtained is compared to a $NO_x$ level previously obtained from an $I_2$-based estimate, and a gain or offset parameter used in the $I_2$-based estimate is adjusted so that the two $NO_x$-level estimates coincide.

To adjust both gain and offset parameters, calibration at two or more different $NO_x$ levels is necessary. Thus, $NO_x$-sensor controller 140 may be configured to initially adjust the gain parameter only, while holding the offset parameter fixed, and then to adjust the offset parameter when data from a range of different $NO_x$ levels becomes available. In some embodiments, adjustment of gain and offset may be executed iteratively, holding one fixed while the other is adjusted. In other embodiments, data representing multiple $NO_x$ levels may be held in memory and fit globally to a two-parameter model. By these and similar methods, $NO_x$ sensor 102 may be self calibrated.

At 218, $NO_x$-sensor controller 140 restores bias voltage $B_2$ to $NO_x$-sensing electrode 138. The $NO_x$ sensor controller may restore the bias by closing switch 146, for example. When bias voltage $B_2$ is restored, current $I_2$ may again reflect the $NO_x$ level in the analyte.

FIG. 3 is a flow chart illustrating example emissions-control procedure 300, which includes $NO_x$-sensor self-calibration procedure 200. In describing the procedure, continued reference is made to the components of FIG. 1. Procedure 300 may be executed by an emissions-control system of a motor vehicle.

At 302, the emissions-control system updates a $NO_x$-sensor self-calibration schedule. In one embodiment, the self-calibration schedule may be based on a fixed time interval, e.g., self calibrate once a day. In other embodiments, the self-calibration schedule may be responsive to an age of the $NO_x$ sensor, a motor-vehicle run time, or on a number of miles accumulated. In some embodiments, the self-calibration schedule may be responsive to some other property of the $NO_x$ sensor that is interrogated by the controller: $I_0$ or $I_1$, for example, where values outside of a predetermined range may point to sensor degradation. In some embodiments, it may be advantageous that self-calibration be delayed for a period of time following a cold start of the motor vehicle, and/or for a different period of time following an exhaust-aftertreatment device regeneration in the motor vehicle. The controller may therefore be configured to delay interrupting bias voltage $V_2$ for such periods of time. In some examples, the self-calibration schedule may be adjusted based on the $NO_x$ level as reflected by $I_2$. For example, the periods of delay indicated above may be responsive to $I_2$.

At 304, the emissions-control system determines whether it is time for $NO_x$-sensor self calibration. If it is not time for $NO_x$-sensor self calibration, then at 306, procedure 300 is paused. Execution of other related and/or unrelated control routines may continue, and in some embodiments, step 306 may include a programmed interrupt to other such control routines. After the pause, execution resumes at 302, where the emissions-control system again updates the $NO_x$-sensor self-calibration schedule, which may depend on changing conditions.

Returning now to step 304, if it is time for $NO_x$-sensor self calibration, then at 200, self-calibration is executed as illustrated by example in FIG. 2. After self-calibration is completed, execution resumes again at step 302.

Note that the example control and estimation routines included herein can be used with various system configurations. The specific routines described herein may represent one or more of any number of processing strategies such as event-driven, interrupt-driven, multi-tasking, multi-threading, and the like. As such, various actions, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, functions, or operations may be repeatedly performed depending on the particular strategy being used. Further, the described operations, functions, and/or acts may graphically represent code to be programmed into computer readable storage medium in the control system.

Further still, it should be understood that the systems and methods described herein are exemplary in nature, and that these specific embodiments or examples are not to be considered in a limiting sense, because numerous variations are contemplated. Accordingly, the present disclosure includes all novel and non-obvious combinations and sub-combinations of the various systems and methods disclosed herein, as well as any and all equivalents thereof.

The invention claimed is:

1. A method of calibrating a response to an exhaust-stream $NO_x$ level in a motor vehicle, the motor vehicle including a $NO_x$ sensor, the method comprising:
   interrupting a bias voltage to an electrode of the $NO_x$ sensor, a current from the electrode responsive to the exhaust-stream $NO_x$ level absent said interrupting; and
   adjusting a motor-vehicle response to the current based at least partly on an attained voltage of the electrode during said interrupting.

2. The method of claim 1, wherein the motor-vehicle response to the current includes reducing a $NO_x$ emission in response to the current.

3. The method of claim 1, wherein the motor-vehicle response to the current includes regenerating an exhaust-aftertreatment device in response to the current.

4. The method of claim 1, wherein the motor-vehicle response to the current includes reducing an air-to-fuel ratio in a combustion chamber in response to the current.

5. The method of claim 1, wherein a duration of said interrupting is responsive to the current.

6. The method of claim 5, wherein the duration increases as the current decreases.

7. The method of claim 1, further comprising sampling the attained voltage of the electrode repeatedly while the current is interrupted.

8. The method of claim 7, further comprising fitting a plurality of voltage samples to a model, the plurality of voltage samples furnished by said sampling.

9. The method of claim 7, further comprising averaging a plurality of voltage samples, the plurality of voltage samples furnished by said sampling.

10. The method of claim 7, further comprising extrapolating from a plurality of voltage samples, the plurality of voltage samples furnished by said sampling.

11. The method of claim 1, wherein interrupting the bias voltage comprises opening a switch, the method further comprising restoring the bias voltage by closing the switch.

12. The method of claim 1 further comprising delaying interruption of the bias voltage for a period following a cold start of the motor vehicle.

13. The method of claim 12, wherein the period is responsive to the current.

14. The method of claim 1 further comprising delaying interruption of the bias voltage for a period following an exhaust-aftertreatment device regeneration in the motor vehicle.

15. The method of claim 1, wherein said interrupting is enacted repeatedly, according to a schedule.

16. The method of claim 15, wherein the schedule is responsive to an age of the $NO_x$ sensor.

17. The method of claim 15, wherein the schedule is responsive to a property of the $NO_x$ sensor interrogated by a controller.

18. The method of claim 1 further comprising adjusting a gain of the $NO_x$ sensor based at least partly on the attained voltage of the electrode during said interrupting.

19. The method of claim 1, further comprising adjusting an offset of the $NO_x$ sensor based at least partly on the attained voltage of the electrode during said interrupting.

20. A method of calibrating a response of a $NO_x$ sensor, the method comprising:
 interrupting a bias voltage to an electrode of the $NO_x$ sensor, a current from the electrode responsive to an exhaust-stream $NO_x$ level absent said interrupting; and
 adjusting a gain of the $NO_x$ sensor based at least partly on an attained voltage of the electrode during said interrupting.

21. The method of claim 20, further comprising adjusting an offset of the $NO_x$ sensor based at least partly on the attained voltage of the electrode during said interrupting.

22. A method for calibrating a response to an exhaust-stream $NO_x$ level in a motor vehicle, the motor vehicle including a $NO_x$ sensor, the method comprising:
 interrupting a bias voltage to an electrode of the $NO_x$ sensor, a current from the electrode responsive to the exhaust-stream $NO_x$ level absent said interrupting;
 adjusting a gain of the $NO_x$ sensor based at least partly on an attained voltage of the electrode during said interrupting; and
 adjusting a motor-vehicle response to the current based at least partly on the attained voltage of the electrode during said interrupting.

* * * * *